(12) United States Patent
Iris

(10) Patent No.: US 8,728,734 B2
(45) Date of Patent: May 20, 2014

(54) METHOD FOR THE RANDOM DIVERSIFICATION OF A GENETIC SEQUENCE WHILE PRESERVING THE IDENTITY OF SOME INNER SEGMENTS OF SAID GENETIC SEQUENCE

(75) Inventor: Francois Iris, Chaville (FR)

(73) Assignee: Pherecydes Pharma, Paris (FR)

( * ) Notice: Subject to any disclaimer, the term of this patent is extended or adjusted under 35 U.S.C. 154(b) by 1116 days.

(21) Appl. No.: 12/528,257

(22) PCT Filed: Dec. 18, 2007

(86) PCT No.: PCT/FR2007/002102
§ 371 (c)(1),
(2), (4) Date: Aug. 21, 2009

(87) PCT Pub. No.: WO2008/093010
PCT Pub. Date: Aug. 7, 2008

(65) Prior Publication Data
US 2011/0053801 A1    Mar. 3, 2011

(30) Foreign Application Priority Data

Dec. 20, 2006   (FR) ..................................... 06 55723

(51) Int. Cl.
*C12Q 1/68*        (2006.01)
*C12P 19/34*       (2006.01)

(52) U.S. Cl.
USPC ........................................ 435/6.12; 435/91.2

(58) Field of Classification Search
None
See application file for complete search history.

(56) References Cited

U.S. PATENT DOCUMENTS

| 6,410,271 B1 * | 6/2002 | Zhu et al. .................... 435/69.7 |
| 2005/0266451 A1 * | 12/2005 | Soderlind et al. ................. 435/6 |

FOREIGN PATENT DOCUMENTS

| EP | 1696037 A | 8/2006 |
| WO | 98/16661 A | 4/1998 |
| WO | 99/23107 A | 5/1999 |
| WO | 02/07742 A2 | 1/2002 |
| WO | 2006/066224 A | 6/2006 |

OTHER PUBLICATIONS

R C Cadwell and G F Joyce, Randomization of genes by PCR mutagenesis, Genome Res. 1992 2: 28-33.*
Yoichi, M. et al. "Alteration of Tail Fiber Protein gp38 Enables T2 Phage to Infect *Escherichia coli* 0157:H7," Journal of Biotechnology, vol. 115, No. 1, Jan. 12, 2005.
Patten, P.A. et al., "Applications of DNA Shuffling to Pharmaceuticals and Vaccines," Current Opinion in Biotechnology, vol. 8, 1997, pp. 724-733.

* cited by examiner

*Primary Examiner* — Kenneth R. Horlick
*Assistant Examiner* — David Thomas
(74) *Attorney, Agent, or Firm* — Browdy and Neimark, PLLC

(57) ABSTRACT

The invention relates to a very general method for the random diversification of a nucleotide sequence S by PCR while preserving the identity of some domains of said sequence S; the invention also relates to a bank of nucleotide sequence thus diversified, and to diversified proteins obtained by the expressions of the nucleotide sequences in an appropriate host.

5 Claims, 8 Drawing Sheets

Figure 1:
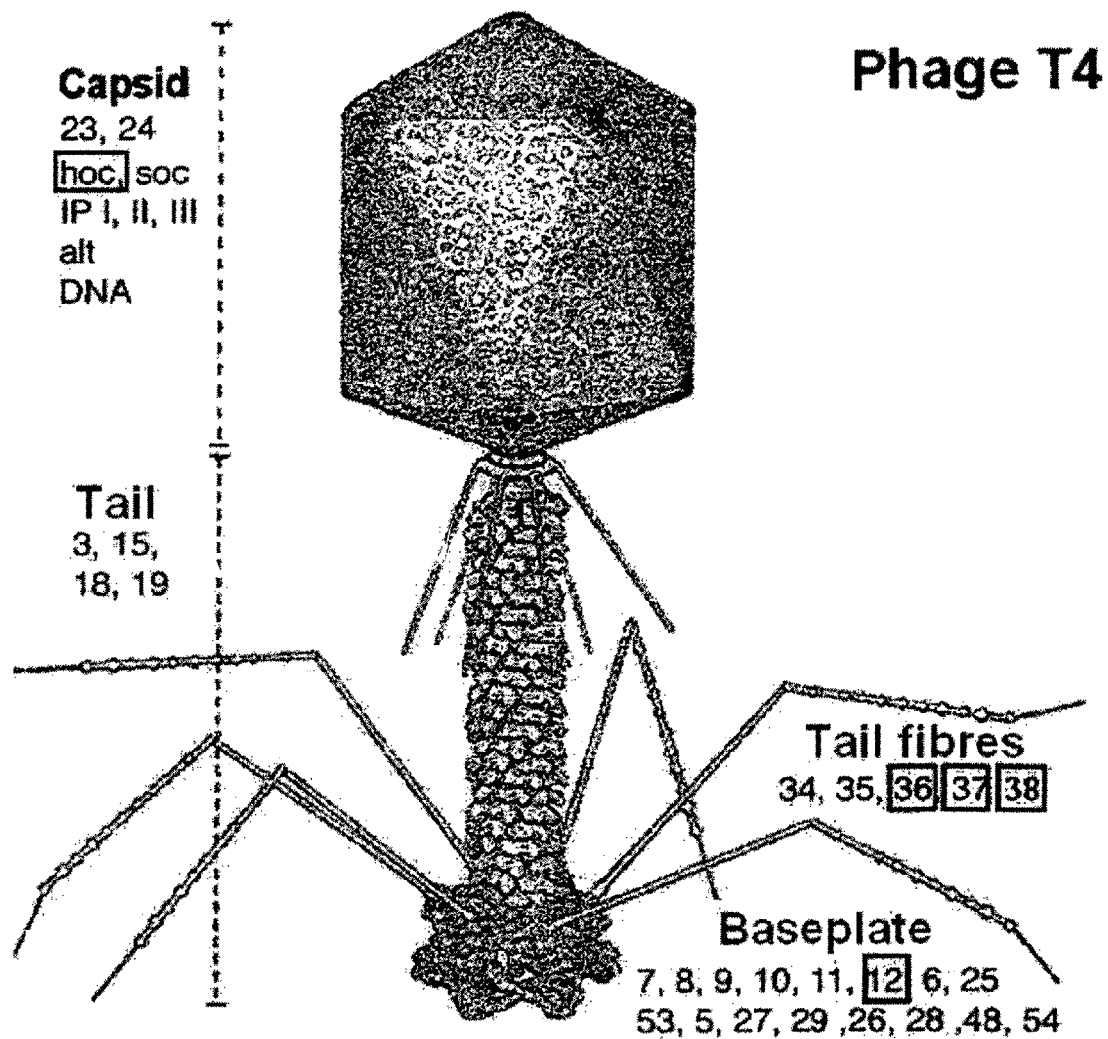
Figure 2:
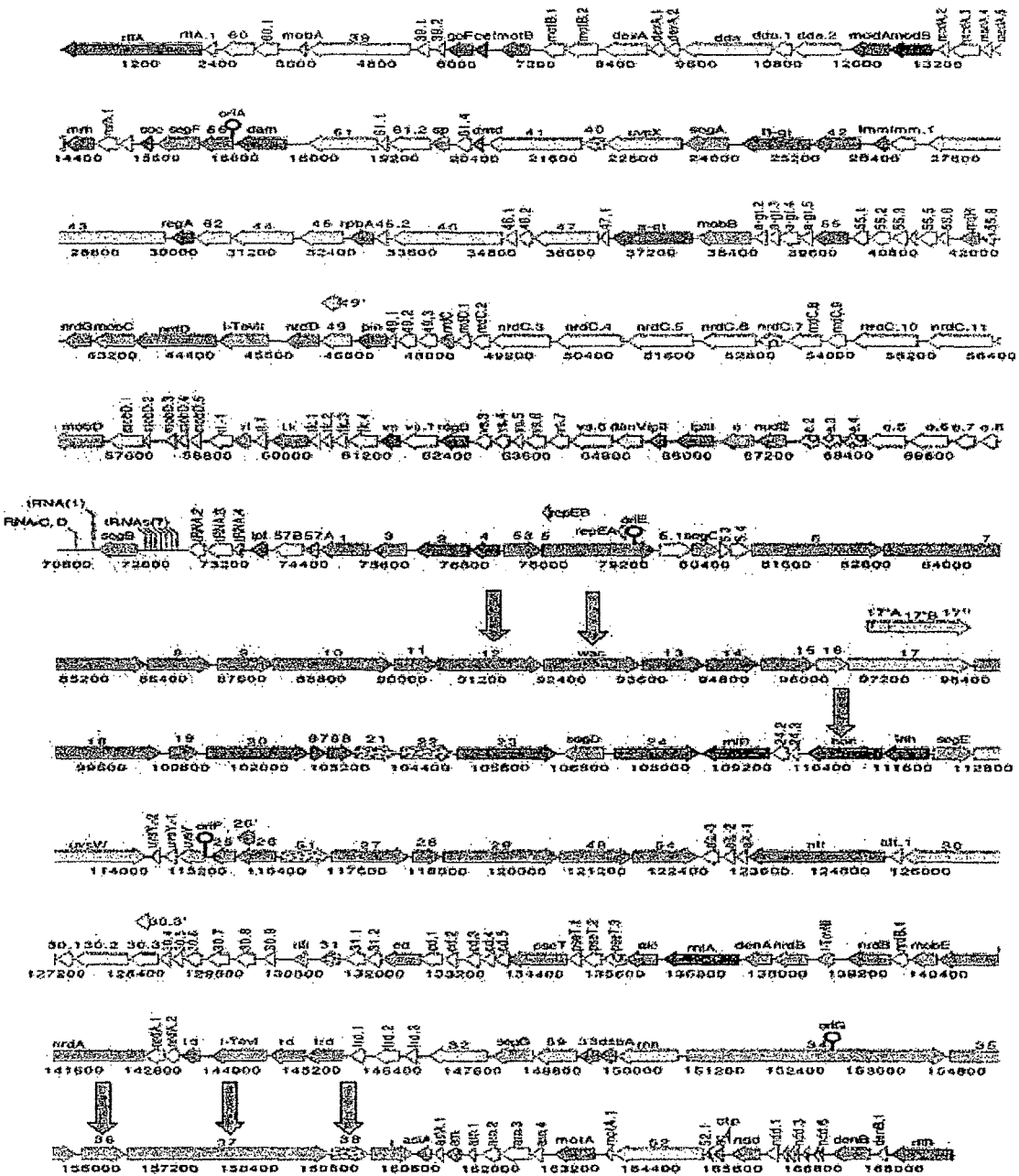

```
  1  MSNNTYQHVSNESRYVKFDPTDTNFPPEITDVHAAIAAISPAGVNGVPDASSTTKGILFI   60
     MSNNTYQHVSNES YV+FDPT +NF    IT+V AA+A+IS GV GVPDAS   KG++ +
  1  MSNNTYQHVSNESVYVEFDPTGSNFDSSITNVQAALASISAYGVKGVPDASEAEKGVIQL   60

61  PTEQEVIDGTNNTKAVTPATLATRLSYPNATETVYGLTRYSTNDEAIAGVNNESSITPAK  120
     TEQEV+DG N+TKAVTPATL  RL YPNA+ET YG+T+Y+T +EAIAG   + SITP K
 61  ATEQEVLDGFNSTKAVTPATLNARLQYPNASETQYGVTKYATQEEAIAGTLDTVSITPLK  120

121  FTVALNNAFETRVSTESSNGVIKISSLPQALAGADDTTAMTPLKTQQLAIKLIAQIAPSE  180
     ++N F TR STE++NGVIKI++   ALAG+DDTTAMTPLKTQQLAIKLI+QIAP+
121  LNQTIDNTFSTRYSTETTNGVIKIATQTAALAGSDDTTAMTPLKTQQLAIKLISQIAPNN  180

181  TTATESDQGVVQLATVAQVRQGTLREGYAISPYTFMNSSSTEEYKGVIKLGTQSEVNSNN  240
     A+ES  GVV+LATVAQ RQGTLREGYAISPYTFMNS +T+EYKGVI+LGTQ+E+NSN
181  DPASESITGVVRLATVAQTRQGTLREGYAISPYTFMNSVATQEYKGVIRLGTQAEINSNL  240

241  ASVAVTGATLNGRGSTTSMRGVVKLTTTAGSQSGGDASSALAWNADVIQQRGGQIIYGTL  300
      VAVTG TLNGRG+T SMRGVVKLTT AG   GD+S ALAWNADVI RGGQ I G+L
241  GDVAVTGETLNGRGATGSMRGVVKLTTQAGVAPEGDSSGALAWNADVINTRGGQTINGSL  300

F1
301  RIEDTFTIANGGANITGTVRMTGG-YIQGN         RTIPVGAIMMWAADSLPSDA   358
     ++.   ANG        +  GG + G+            +PVG I M+A DS P
301  NLD--HLTANG------IWSRGGMWKNGD          SERVPVGTIQMFAGDSAP-PG  350
        D1                      D2
359  WRF       ASDCPLYASRIGTRYGGNPSNPGL    FVRGSGRGSHLTNPNVNGND   418
     W              P Y + +GTR+GG+ +NPG+   FVRG+G GSH+ N    G D
351  WVL       GDQFPDYRNVVGTRFGGDWNNPGI     FVRGAGTGSHILNN--RGQD  408
        D3              D4
419  QF       VGCTGGYVGEVQIQQMS       GEHDDLGA-FGNTRRSNFVGTRKGLDW  477
     +         VGC G +VG VQ QQMSY      +GE    A FG.+    ++GTRK DW
409  GY       VGCDGMHVGGVQAQQMSY      GEFQRHEAPFGASVYQGYLGTRKYSDW  468

F2
478  DNRSYFTNDGYEIDPESQRNSKYTLNRPELIGNETRPWNISLN       525
     DN SYFTNDG+E+    R++  TLNR  LIG ETRPWNISLN
469  DNASYFTNDGFELG--GHRDATGTLNREGLIGYETRPWNISLN       514
```

Fig. 5

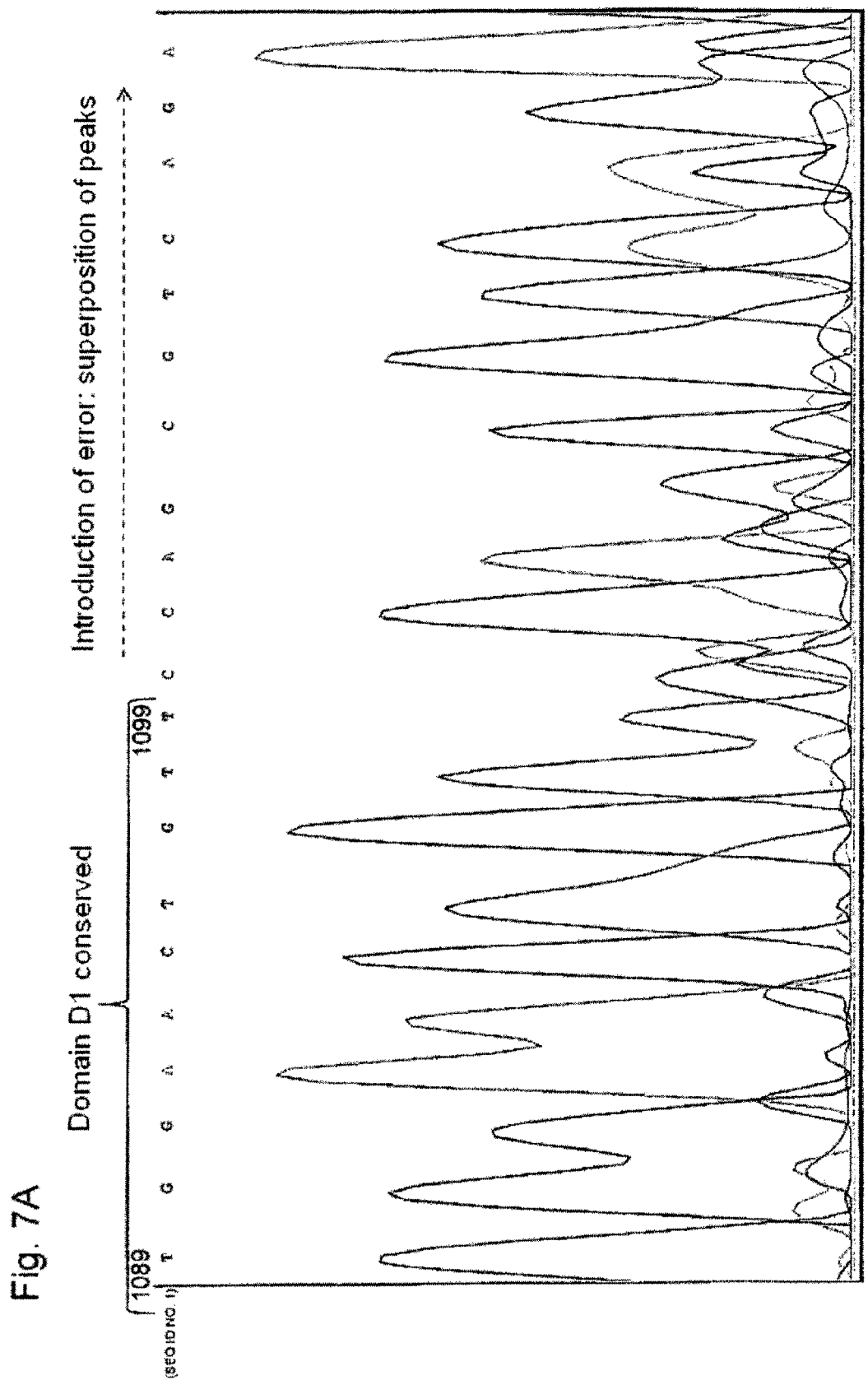

METHOD FOR THE RANDOM DIVERSIFICATION OF A GENETIC SEQUENCE WHILE PRESERVING THE IDENTITY OF SOME INNER SEGMENTS OF SAID GENETIC SEQUENCE

The present invention relates to a very general method for the random diversification of a nucleotide sequence S by PCR, while preserving the identity of certain domains or segments of said sequence, a bank of nucleotide sequences thus diversified, and more particularly a bank of sequences encoding target proteins of modified bacteriophages.

The bacteriophages are viruses capable of infecting bacteria specifically and of replicating therein. Their existence was demonstrated at the beginning of the XXth century by the Briton Frederick Twort and the Quebecker Félix d'Hérelle.

The bacteriophages occupy all the ecological niches where there are bacteria. They occur in two main forms: the lysogenic form, by which they can remain quiescent inside their host, or else in lytic form, when they replicate actively with lysis of the bacterial cell. The lytic form causes the bacteriophages to be released in large numbers in the environment in an infectious form.

In order to maintain their infectious character with respect to their hosts, which sometimes undergo rapid mutations, the bacteriophages must constantly evolve. Accordingly, they naturally have a high degree of specialization for the bacterial species that they parasitize and are very diversified.

Since their discovery, the bacteriophages were regarded as a means of combating bacterial infections, well before the era of antibiotics.

Thus, the procedure consisting of identifying bacteriophages in nature that are specific to a pathogenic bacterium in order to treat patients infected with this bacterium was developed in Russia and in the countries of the former Soviet bloc during the first half of the XXth century.

However, antibiotics, which are generally of a broader spectrum, found general application on a massive scale in the second half of the XXth century, without all the possibilities offered by bacteriophages having been exploited.

Today, faced with the appearance of bacterial strains that are multiresistant to antibiotics, and in view of the difficulties encountered by the scientific community in developing new antibiotics, the bacteriophages are arousing renewed interest for the treatment of bacterial infections that are difficult to eradicate, in particular in the case of nosocomial contaminations [Thiel, K., *Nature Biotechnology*, 2004, 22:31-36].

However, certain difficulties still persist in the use of bacteriophages, in particular from the fact that bacteria can evade the bacteriophages by masking or modifying the constituent elements of their outer wall.

The replication cycle of the bacteriophages in fact requires a stage of recognition and of adhesion of the bacteriophage to the wall of the host bacterium, which determines whether it is possible for the bacteriophage to infect the bacterium, i.e. to inject the genetic material contained in its capsid inside the cytoplasm of the bacterium.

Bacteriophage T4, for example, is a bacteriophage that infects bacteria of the *Escherichia coli* type, whose replication cycle lasts about 30 minutes at 37° C. This replication cycle begins immediately after recognition of the host bacterium by the bacteriophage, by the stage of absorption and penetration. It is reflected in the immediate cessation of expression of the genes of the host bacterium, synthesis of the enzymes necessary to the replication of the phage, 5 minutes after infection, then replication of the DNA (starting after 10 minutes) and formation of the virus (starting after 12 minutes). The replication cycle leads to disruption of the bacterium (after 30 minutes) and release to the environment of about fifty bacteriophages per lysed bacterium.

Figure 3:
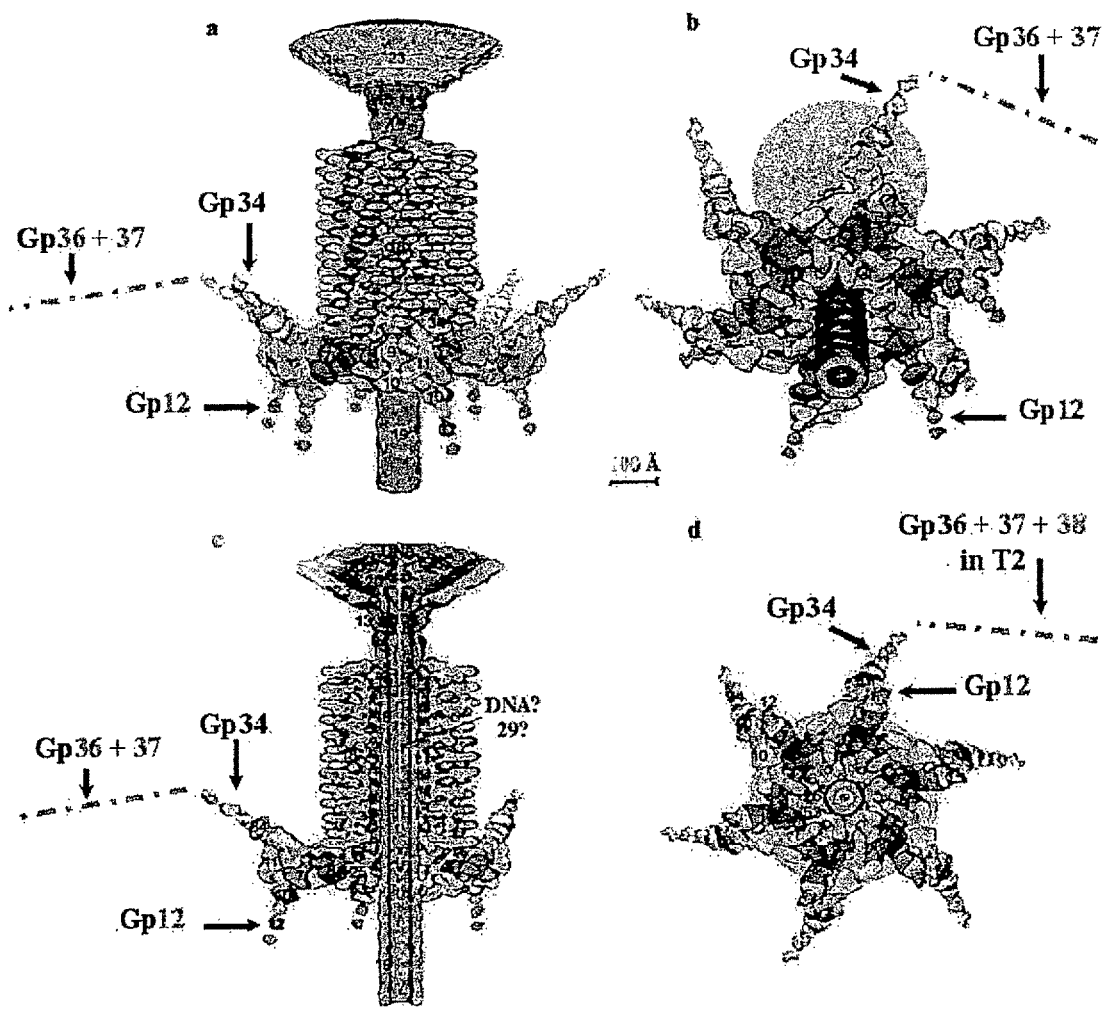
Figure 4:
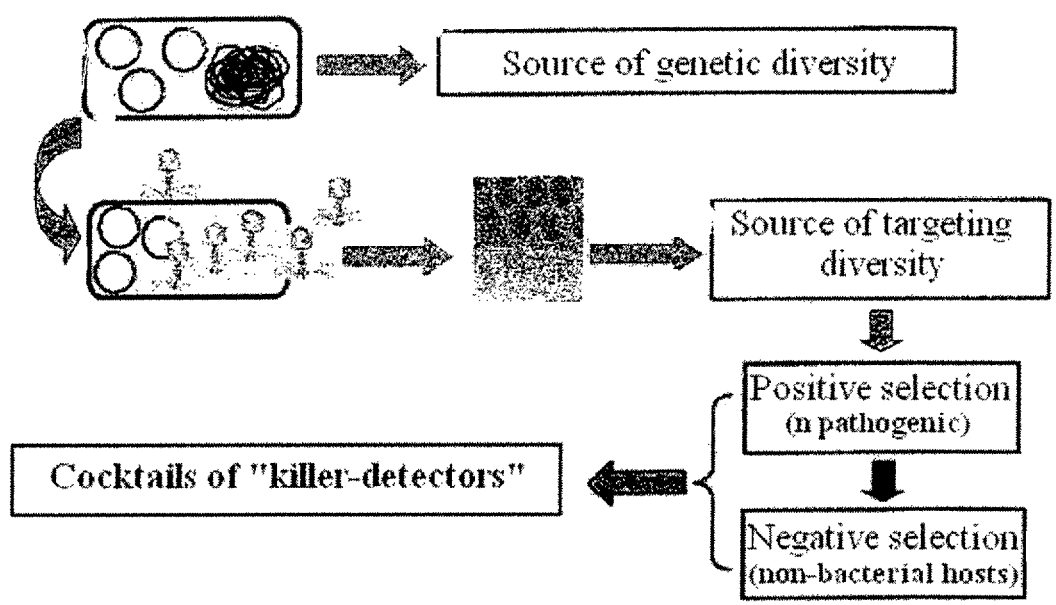

Adhesion to the bacterium is essentially provided by the proteins of the baseplate serving as anchoring for the bacteriophage, and recognition is provided more particularly by proteins forming the peripheral filaments, called "tail fibres". Nevertheless, the tail-fibre and baseplate proteins can be involved simultaneously in recognition and in adhesion of the bacteriophage to the bacterial wall. All of these so-called "target" proteins are represented in FIGS. 1 and 3 of the present application.

Among the proteins involved in this recognition or adhesion in phage T4, we may mention more particularly glycoproteins GP12 of the baseplate, and glycoproteins GP36, GP37 and GP38 of the tail fibres.

In order to limit the emergence of bacteria that are resistant to the recognition system of the bacteriophages, generally the simultaneous use of different forms of bacteriophages capable of targeting one and the same bacterium is proposed.

These bacteriophages are found in nature or are obtained from collections, together forming what is known as "a cocktail of bacteriophages".

However, for the development of these cocktails of bacteriophages it is best if the bacteriophages of which they are composed are selected individually and rigorously, in particular ensuring that these bacteriophages are lytic and not lysogenic or partially lysogenic, as is often the case with bacteriophages obtained from the natural environment.

The need to test the bacteriophages individually to be certain of their real efficacy makes the development of the cocktails of bacteriophages long and arduous, especially as a different cocktail must be provided for each bacterium considered.

Application WO 01/51066 describes such a preparation of bacteriophages comprising six different bacteriophages used as a preservative of fresh foodstuffs for destroying the bacterium *Listeria monocytogenes*, which is responsible for listeriosis. This natural preparation is packaged in an atomizer for spraying on meat or on dairy products. It is harmless to humans, animals or plants, as the bacteriophages can only infect bacteria of the genus *Listeria* and not the cells of multicellular organisms.

To overcome the problems posed by the selection of natural bacteriophages, a method is proposed in application WO 06/066224 for obtaining bacteriophages whose target proteins are modified with a view to specifically targeting a given virulence factor. The virulence factors are molecules described as being necessary for the bacterium to develop an infection. These molecules are regarded as stable elements, less susceptible to variation in the course of infection than the elements of external structures, such as lipopolysaccharides for example. More particularly, this method proposes selecting a protein originating from a natural bacteriophage (for example GP37 of phage T4) capable of recognizing a virulence factor described in the literature (for example OmpC of *E. coli*), of transferring the gene encoding this protein in a lambda bacteriophage and using the lambda bacteriophage for modifying said protein. The modification of the protein comprises effecting exchanges among the various domains involved in the recognition of the virulence factor (for example the His domains of GP37). The lambda phages are then tested for their capacity for adhering to the virulence factor targeted. This method, which is similar to the technique of phage display, makes it possible to isolate different variants of the lambda bacteriophage capable of targeting the virulence factor, and thus provide various target proteins. The genes corresponding to these various target proteins can then be transferred into infectious bacteriophages. These bacteriophages can then constitute cocktails of phages that are active with respect to the bacterium bearing the virulence factor targeted initially.

This method represents an advance in the production of diversified bacteriophages for the development of cocktails of bacteriophages. Nevertheless, such cocktails still only relate to the bacterial species expressing the virulence factor targeted initially.

Therefore this method can only be employed for cultivable pathogenic bacteria for which prior identification of the virulence factors was possible.

To make the use of the bacteriophages more universal, it would be useful to have bacteriophages that are infectious with respect to a larger number of species, for example by creating bacteriophages whose infectivity spectrum has been modified or extended. Such bacteriophages could be used against new bacterial species, in particular against emergent pathogenic bacteria or those responsible for nosocomial infections.

Nevertheless, the production of phages with a modified infectivity spectrum comes up against the technical constraint that the production of bacteriophages is dependent on the host bacterium in which the bacteriophage is transformed and then multiplied. The stages of genetic modification of phages generally comprise several stages of replication in a single host bacterium.

In the experiments described in the documents of the prior art cited above, numerous replication cycles are necessary for modifying the bacteriophages used for targeting the virulence factors. Homologous recombination, which is the technique encountered most often for transforming the genome of bacteriophages, involves numerous successive cycles of replication and selection in the bacterium. Now, the modified bacteriophages, if they succeed in acquiring the ability to infect hosts different from their usual hosts, may also lose the ability to infect the host used for their replication. Therefore they are eliminated from selection and evade the experimenter. As a result there is a considerable loss of diversity of the modified phages that can be obtained.

To overcome the aforementioned difficulties, the present invention proposes a novel method consisting of random diversification of nucleotide sequences, in particular those encoding the target proteins of bacteriophages, by inserting randomly produced DNA sequences in their genes.

This method is particularly useful for producing copies of genes containing randomly mutated segments, in particular with a view to cloning them in expression vectors or homologous recombination vectors.

The present method according to the invention was developed originally for diversifying the target proteins of bacteriophages and so as to obtain, by homologous recombination, recombinant bacteriophages with variable host specificity.

However, it is not to be limited just to the area of bacteriophages, as it can be applied to any sequence of DNA or of RNA.

There are a great many fields of application, in particular in the medical field, as we wish to modify a genetic sequence randomly in its variable domains, while preserving the identity of the constant domains, which are generally essential for the functionality of the protein.

The method according to the invention is described in detail below, together with its more particular application in the area of bacteriophages.

FIG. 1: representation of bacteriophage T4 showing the different constituent elements of the bacteriophage. The proteins considered within the scope of the present invention are shown in boxes.

FIG. 2: representation of the complete genome of bacteriophage T4. The genes mentioned in the present application are indicated with an arrow perpendicular to the open reading frames.

FIG. 3: three-dimensional representation of the baseplate of the bacteriophage and of the tail fibres involved in recognition and adhesion of the bacteriophage to the host bacterium, visualizing the target proteins modified according to the method of the invention.

FIG. 4: schematic diagram summarizing the principle of production of a bank of recombinant bacteriophages according to the invention. The box at top left shows a host bacterium comprising 3 homologous recombination vectors for introducing oligonucleotides whose sequence is produced randomly in three genes encoding the target proteins of the bacteriophage. These vectors represent DNA constructs in the sense of the present invention, bearing considerable genetic diversity. After infection by a bacteriophage and homologous recombination, a large number of bacteriophages (bank of bacteriophages) having modified target proteins are obtained, forming "a source of targeting diversity". The bacteriophages obtained are screened with respect to potential new hosts (positive selection) in order to select bacteriophages capable of infecting said hosts. They can also be tested on non-bacterial hosts (eukaryotic cells) to ensure that they are not dangerous to humans or to animals.

FIG. 5: comparison of the polypeptide sequence of GP12 of bacteriophage T4 (top line) and of its homologue present in bacteriophage RB 69 (bottom line) according to the BLAST protocol. The amino acids common to both proteins are indicated on the intermediate line. The symbol "+" signifies that the amino acids are similar. The N-terminal portion shown in the box corresponds to the domain of these two proteins that permits anchoring of the bacteriophage on the wall of the bacterium. It is this anchoring domain that is mutated randomly and then inserted by homologous recombination in the genome of the phage according to the invention. The inner segments D1 to D4 correspond to the sequences of the protein that are conserved in the course of the method of random diversification applied by PCR according to the invention.

FIG. 6: this diagram summarizes the stages of the PCR method employed according to the invention for obtaining, in particular, a copy of the anchoring domain of gp12 in which oligonucleotides produced randomly are inserted. The inner segments D1 to D4 whose sequence identity we wish to conserve are shown as rectangles. These domains correspond to those mentioned in FIG. 5 above. The two outer segments delimit the sequence of the anchoring domain of gp12. A: the anchoring domain of gp12 is amplified by high-fidelity PCR. B: 4 error-prone PCRs are carried out independently using the aforementioned oligonucleotides. C: The amplification products obtained in B are purified and assembled in one and the same high-fidelity PCR reaction. Said amplification products overlap so that it is possible to assemble the various fragments, but provided that the domains D1 to D4 are sufficiently conserved to permit hybridization of the primers used. D: The PCR performed in stage C results in two fragments PA-1 and PB-1, which are assembled using the primers corresponding to the outer segments of the anchoring domain of GP12. Finally, we obtain a copy of the anchoring domain of gp12 whose sequence has been modified randomly except at the level of domains D1 to D4, whose identity was conserved.

The primers used in the example of application were returned to each of the stages mentioned in this diagram.

Figure 7B:
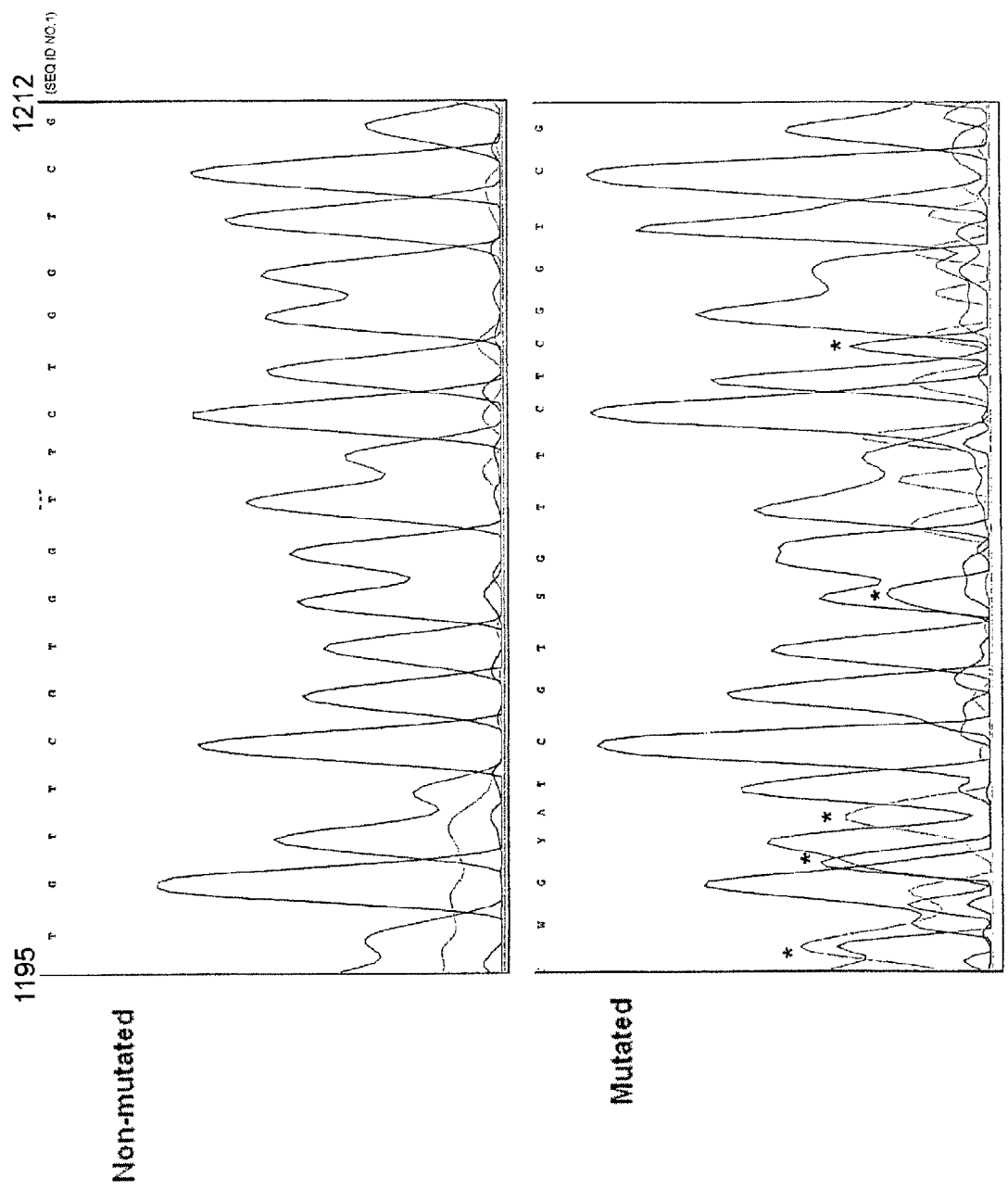

FIG. 7: Sequencing profile obtained directly on the PCR products (gp12-Mut) obtained according to the method of the invention. The profiles were established using the free ApE analysis software based on the data obtained from an automatic sequencer. A: sequencing of the portion of gp12 located between nucleotides 1089 and 1110 (SEQ ID No. 1). The left-hand part that is conserved corresponds to the 3' part of domain D1 (nucleotides 1089 to 1099). The right-hand part shows a superposition of peaks taking into account the random mutations that are produced in the course of PCR in the region located immediately downstream of D1 (nucleotides 1100 to 1110). B: comparison of the sequencing performed in a non-mutated region of gp12 located between nucleotides 1195 and 1212 of SEQ ID No. 1 (top) and performed for the same region on the PCR products obtained according to the method (bottom). The sequenced region is located between the conserved domains D1 and D2. The presence of superposed peaks is observed (bottom), which take account of the random insertion of nucleotides in the initial sequence of gp12.

DESCRIPTION OF THE METHOD OF DIVERSIFICATION OF GENETIC SEQUENCES ACCORDING TO THE INVENTION

The present invention therefore relates more particularly to a method of PCR permitting random mutation of a nucleotide sequence S, delimited at its 5' and 3' ends by two segments F1 and F2, while preserving the identity of at least one inner segment D of said nucleotide sequence, characterized in that it comprises the following stages:

i) an error-prone PCR is performed on the whole of sequence S using primers corresponding to segments F1 and F2, by which sequence S will be mutated randomly on its entire length;

ii) the amplification products obtained are eluted;

iii) high-fidelity PCR is carried out starting from the amplification products eluted in stage ii), using the primer pairs corresponding respectively to at least F1 and D, and F2 and D, in order to amplify the F1-D and D-F2 regions of S mutated in stage i) whose inner segment D has preserved its identity;

iv) high-fidelity PCR is performed starting from the amplification products obtained in stage iii) using the primers corresponding to F1 and F2;

v) the PCR products obtained, whose size corresponds to that of nucleotide sequence S, are purified.

A primer according to the invention is a single-stranded nucleic acid, capable of hybridizing with a portion, or the whole, of one of the DNA strands forming all or part of sequence S. A primer is said to be a "sense primer" when its nucleotide chain reproduces, with the exception of some nucleotides, a part of the coding strand of S. A primer is said to be an "antisense primer" of S, when its nucleotide chain reproduces, with the exception of some nucleotides, a part of the non-coding strand of S.

When a primer is described as "corresponding to" a given segment of sequence S, this signifies that it can be sense or antisense relative to a part of S taken in its form of double-stranded DNA molecule.

The method of PCR according to the invention involves the use, more particularly, of sense and antisense PCR primers in the manner described below and in the examples of the present application. Thus, according to the invention:

i) an error-prone PCR is performed on the whole of sequence S using at least two primers of which one is sense and the other antisense respectively of segments F1 and F2, so as to amplify sequence S, introducing mutations into it randomly;

ii) the amplification products obtained, which correspond to randomly mutated copies of S, are purified;

iii) high-fidelity PCR is performed starting from the amplification products purified in stage ii), using as sense and antisense primer pairs, respectively, at least:

a sense primer corresponding to F1 and an antisense primer of segment D, in order to amplify region F1-D of the mutated copies of S, a sense primer corresponding to segment D and an antisense primer of F2, in order to amplify region D-F2 of the mutated copies of S, iv) the amplification products obtained in stage iii), which consist of copies of segments F1-D and D-F2 of sequence S mutated in stage i), in which segment D has preserved its identity, are purified;

v) high-fidelity PCR is performed starting from the amplification products purified in stage iv) using sense and antisense primers corresponding respectively to F1 and F2.

vi) the PCR products obtained, which correspond to the nucleotide sequences S mutated in stage i), in which segment D has preserved its identity, are purified.

This method is particularly advantageous when we wish to preserve the identity of several inner domains $D_N$ of nucleotide sequence S (as is the case for protein GP12), N being regarded as an integer greater than or equal to 1.

The method thus comprises the following stages:

i) an error-prone PCR is performed on the whole of sequence S using at least two primers of which one is sense and the other antisense respectively of segments F1 and F2, so as to amplify sequence S, introducing mutations into it randomly;

ii) the amplification products obtained, which correspond to randomly mutated copies of S, are purified;

iii) high-fidelity PCR is performed starting from the amplification products purified in stage ii), using as sense and antisense primer pairs, respectively, at least:

a sense primer corresponding to F1 and an antisense primer of $D_N$, in order to amplify at least region F1-$D_N$ of the mutated copies of S, and a sense primer corresponding to $D_N$ and an antisense primer of F2, in order to amplify at least sequence $D_N$-F2 of the mutated copies of S;

iv) the amplification products obtained in stage iii), which consist of copies of segments F1-$D_N$ and $D_N$-F2 of sequence S mutated in stage i), in which the sequence of segment D has preserved its identity, are purified;

v) high-fidelity PCR is performed starting from the amplification products obtained in stage iv) using at least one pair of sense and antisense primers of F1 and F2;

vi) the PCR products obtained in stage v), which correspond to randomly mutated nucleotide sequences of said insert in which at least the sequence of segment $D_N$ has preserved its identity, are purified.

The same method can also be described as follows, considering the successive domains $D_N$ and $D_{N+1}$:

i) an error-prone PCR is performed on the whole of sequence S using primers corresponding to segments F1 and F2, by which sequence S will be mutated randomly on its entire length;

ii) the amplification products obtained are eluted;

iii) high-fidelity PCR is performed starting from the amplification products eluted in stage ii), using the primer pairs corresponding respectively to at least F1 and $D_{N+1}$, and F2 and $D_N$, in order to amplify at least the regions F1-$D_{N+1}$, and $D_N$-F2 of S mutated in stage i), whose inner segments $D_{N+1}$ and $D_N$ have preserved their identity;

iv) high-fidelity PCR is performed starting from the amplification products obtained in stage iii) using the primers corresponding to F1 and F2;

The domains can also be denoted $D_{N-1}$ and $D_N$:

i) an error-prone PCR is performed on the whole of sequence S using at least two primers of which one is sense and the other antisense respectively of segments F1 and F2, so as to amplify sequence S, introducing mutations into it randomly;

ii) the amplification products obtained are purified;

iii) high-fidelity PCR is performed starting from the amplification products purified in stage ii), using as sense and antisense primer pairs at least:

a sense primer corresponding to F1 and an antisense primer of $D_N$, in order to amplify region F1-$D_N$ of the mutated copies of S in which segment $D_N$ has preserved its identity;

an antisense primer of F2 and a sense primer corresponding to $D_{N-1}$, in order to amplify the mutated region $D_{N-1}$-F2 of S in which segment $D_{N-1}$ has preserved its identity;

iv) high-fidelity PCR is performed starting from the amplification products obtained in stage iii) using at least one pair of sense and antisense primers of F1 and F2;

vi) the PCR products obtained in stage v), which correspond to randomly mutated nucleotide sequences S, in which at least the sequences of segments $D_N$ and $D_{N-1}$ have preserved their identity, are purified.

According to a preferred aspect of the invention, this method can be used for introducing randomly produced oligonucleotides in certain variable domains of the sequences encoding the target proteins of bacteriophages. The target proteins of the bacteriophage are defined as proteins that participate in the recognition and adhesion of the bacteriophage to the host bacterium. These proteins are preferably selected from those constituting the tail fibres or the baseplate of phage T4. A protein that is particularly suitable for the method according to the invention is protein GP12 of the baseplate, whose nucleotide sequence corresponds to SEQ ID No. 1. Other preferred target proteins are GP36, GP37 or GP38 constituting the distal portion of the tail fibres. Of course, proteins that are homologues of those mentioned above, present in other bacteriophages, are also preferred.

By "homologous sequence" is meant sequences having at least 50% identity with the latter, preferably at least 70%, more preferably at least 90% present in two organisms of different species.

The present application gives the example of modification of protein GP12 of bacteriophage T4, which is particularly preferred according to the invention. Protein GP12 has an anchoring domain, into which it is desirable to introduce variability while maintaining the integrity of certain segments designated D1 to D4 (FIG. 5), said segments corresponding to conserved domains in the homologous proteins of type-T bacteriophages.

Preferably, it is the segments of the genes of the proteins corresponding to the protein domains involved in the functions of adhesion or recognition that are modified, and more preferably the segments corresponding to variable domains.

By "variable domain" is meant the segments of a sequence that are less conserved when two sequences that are homologous to one another are compared.

Conversely, it is preferable to preserve the identity of the most conserved domains, which are generally indispensable to the functionality of the proteins that are encoded, in each case, by these sequences.

The PCR protocols used according to the invention are standard protocols well known by a person skilled in the art. It is the manner in which they are applied that constitutes the special feature of the invention.

By "error-prone PCR" is meant a polymerase chain reaction carried out in conditions that do not permit faithful replication of the DNA sequences. This type of reaction can be performed using a conventional polymerase of type Taq in low-stringency conditions and in the presence of manganese salts, as described in the literature [Cadwell, R. C. et al. 1992, *Randomization of genes by PCR mutagenesis, PCR Methods Appl.,* 2:28-33].

High-fidelity PCR is, in contrast, a polymerase chain reaction permitting amplification of a DNA matrix with a very low replication error rate. This type of reaction can be obtained by employing, for example, a Pfu type of polymerase in stringent conditions, as described in the literature [Inmis, M. A. et al. Eds., PCR Protocols: a guide to methods and applications, 1989, Academic Press].

The reactions of high-fidelity PCR mentioned in stage iii), which permit amplification of the sub-regions of sequence S located between the conserved segments, are preferably carried out separately.

In the examples of the present application the letter F denotes a "sense" primer (or "forward" primer) and the letter R denotes an "antisense primer" (or "reverse" primer).

The present method can be applied to any nucleotide sequence for which we wish to vary certain segments selectively and randomly.

The method according to the invention can find applications in many therapeutic areas.

Its application is in fact particularly useful when we wish to modify a protein's spectrum of activity, or of interaction with a ligand, by randomly modifying particular domains of its genetic sequence.

Thus, the invention envisages, for example, that sequence S is a genetic sequence encoding a protein of interest.

According to a preferred aspect of the invention, the protein of interest is a target protein of a bacteriophage, such as protein GP12 of a type T bacteriophage.

However, it can also be any protein of therapeutic or diagnostic interest for which we wish to vary the active sites or the interaction domains, for example a ligand protein for which we aim to modify the specificity with respect to a receptor or alternatively an immunoglobulin for which we aim to modify the variable or hypervariable domains for the purpose of detecting antibodies.

The present application has no known limitations from the standpoint of the numerous applications that the modification of a genetic sequence according to the invention allows us to envisage.

When sequence S is in the form of RNA, the present method can be preceded by a stage of reverse transcription for obtaining a copy of said sequence in the form of a polynucleotide according to the usual protocols.

The amplification products obtained according to the particular method of the invention constitute a bank of randomly diversified nucleotide sequences S for which the identity of the inner domains $D_N$ has been preserved.

The invention therefore also relates to the PCR products obtained according to the invention, which are characterized in that they consist of polynucleotide variants resulting from the random mutation of sequence S and characterized in that one or more inner domains D of said sequence S have been conserved.

In other words, the invention makes it possible to obtain a bank of polynucleotides constituted by variants of a nucleotide sequence S randomly mutated by PCR, characterized in that said variants contain one or more inner segment(s) D of said sequence S that are intact or whose identity has been preserved.

In general the inner domains $D_N$ preserve, according to the method of the invention, more than 50% identity relative to their original sequence in the wild-type protein, preferably more than 70%, and more preferably more than 90%, or even more than 99%, according to the PCR conditions used, in particular the conditions of high-fidelity PCR carried out in stages iii) and v) of the method according to the invention.

The polynucleotide variants constituting the bank of nucleotide sequences according to the invention can be cloned directly in expression vectors, or more preferably in homologous recombination vectors, which a person skilled in the art has at his disposal, and can form a set of constructs according to the invention.

The method according to the invention makes it possible in particular to overcome the difficulty of partially mutating a gene randomly. In fact, in the prior art this necessitated producing oligonucleotides randomly and then assembling said oligonucleotides by cloning at the parts of the sequence of the gene whose identity we wished to preserve. Now, when several oligonucleotides must be inserted at different points of the gene, this work is very arduous and the result in terms of diversity of the sequences obtained is disappointing.

The DNA constructs according to the invention, considered in their entirety, thus make it possible more particularly for a very large number of different nucleotide sequences encoding modified proteins to be incorporated in the genome.

The invention therefore also relates to a method of diversification of a protein encoded by a nucleotide sequence S, characterized in that the polynucleotide variants of said nucleotide sequence S contained in a PCR product or a bank of polynucleotides as defined above are expressed in a suitable expression host.

This method can in particular comprise:
  cloning, in an expression vector, the PCR products obtained in stage vi) of the method according to the invention, which correspond to the mutated nucleotide sequences S in which at least one domain D has remained identical, then
  transforming a host cell permitting expression of the polypeptide encoded by sequence S,
  expressing, in said host cell, said mutated nucleotide sequences S in which at least one domain D has remained identical, to obtain diversified proteins, and
  purifying the various proteins obtained.

These stages are carried out by techniques well known by a person skilled in the art [Sambrook J., Russel D. W. (2001) Molecular Cloning, a Laboratory Manual, CHSL Press].

Once they are translated into protein, the nucleotide sequences contained in the aforementioned bank can result in the expression of proteins displaying a diversity of polypeptide sequences produced randomly including inner domains 1N whose identity of the polypeptide sequence is preserved.

In this respect the invention relates to a bank of proteins resulting from the expression of a bank of nucleotide sequences as stated above, said proteins displaying a diversity of polypeptide sequences produced randomly including inner segments $D_N$ whose identity has been preserved.

The present method therefore permits the targeted modification of any protein for which we wish to change certain functional specificities, by randomly varying the sequences of said proteins involved, for example, in interactions with ligands, catalytic activities, toxicity or transport.

Application of the Diversified Sequences Obtained According to the Method of the Invention to the Transformation of Bacteriophages Mutated in their Target Proteins:

According to a preferred aspect of the invention, the amplification products obtained are inserted in the genes of the bacteriophage encoding its target proteins, by means of homologous recombination.

The DNA constructs preferred according to the invention preferably comprise:
  a region permitting the duplication of said construct in a host bacterium;
  a region permitting homologous recombination in the genome of the bacteriophage at the level of a gene encoding a target protein, said region comprising two DNA sequences homologous to the sequences of said gene encoding a target protein, which delimit an insertion segment including an oligonucleotide whose sequence is produced randomly, preferably according to the method using PCR described above.

According to a preferred aspect of the invention, the region permitting homologous recombination comprises all or part of the gene encoding the target protein, preferably the whole of the sequence of the gene.

Preferably, this second region consists of an amplification product that can be obtained according to the method of random mutation presented above.

According to a preferred aspect of the invention, several genes encoding target proteins of the phage are mutated simultaneously by homologous recombination according to the method of the invention. To achieve such a result, the invention envisages transforming the host bacterium successively using various vectors, each targeting a different gene.

The preferred vectors permitting simultaneous modification of genes GP12, GP37 or GP38 of bacteriophage T4 according to the invention in the host bacterium *E. coli* are, for example, the vectors pACYC184 (ATCC 37033), pBAD18-K (ATCC 87397) and RR1 (ATCC 87076). Such vectors offer the advantage that they possess markers conferring resistance to various antibiotics and do not share common nucleotide sequences capable of causing recombinations between the different vectors once the latter are incorporated in the host bacterium.

A bacteriophage according to the invention is, preferably, a natural or modified, lytic bacteriophage.

Preferably, the bacteriophage used is a T type phage, such as bacteriophages T4, T5, T6 and T7, well known by a person skilled in the art and more particularly phage T4, whose genome has been sequenced [Miller, E. S. et al., Bacteriophage T4 genome, *Microbial Mol. Biol. Rev.*, 2003, 67(1):86-156]. The complete sequence of the genome of the bacteriophage is available in Genbank (AF 158101).

A host bacterium according to the invention is a bacterium commonly used for replicating the phage that we aim to modify. Preferably, the host bacterium is a strain that can be transformed using a DNA construct according to the invention permitting the phage to be modified by homologous recombination.

By transforming this host bacterium using the DNA constructs according to the invention, we have at our disposal one or more banks of transformed host bacteria. Each of the bacteria in this bank potentially contains a construct capable of transforming, by homologous recombination, one or more of the target proteins of the phage in different ways.

Such a bank of host bacteria offers the advantage that it can be multiplied and stored. It constitutes a renewable intermediate product that can be used for the production of recombinant bacteriophages whose target proteins are randomly modified.

Using the method according to the invention, it is possible to obtain a very diversified set of recombinant bacteriophages.

These bacteriophages form a bank of bacteriophages in the sense of the present invention.

So that a bank of bacteriophages according to the invention covers the largest possible number of different bacteriophages, it is necessary to employ a sufficient number of transformed host bacteria, as it is this number that determines the number and diversity of the phages harvested.

If this number is sufficient, a bank of bacteriophages according to the invention contains as a minimum, at least $10^6$, preferably $10^8$, more preferably $10^{10}$ different variants of one and the same bacteriophage, said variants differing by the sequence of at least one of their target proteins.

The diversity of the bacteriophages in the bank according to the invention can be demonstrated by a simple calculation of the count.

Thus, if we assume that preferably:
3 genes encoding target proteins are modified; by the insertion of at least 3 oligonucleotides composed of random sequences of at least 12 nucleotides; and that
⅓ of the nucleotide sequences impose a polypeptide modification at the level of the target proteins; and that
only 3 of the 4 bases (A, T, C, G) are capable of producing a mutation relative to the original protein;
we then obtain a minimum of $3^{24}$ possibilities of mutations at the polypeptide level, giving a count of some $2.8 \times 10^{11}$ potentially different bacteriophages.

The following experimental protocols are for the purpose of illustrating the invention as examples without limiting the claimed scope of the invention.

Preparation of the Sequences of Variants of gp12, gp37 and gp38 of Phages T4

What follows describes the procedure used for gp12, but it can be transferred without difficulty for a person skilled in the art to the modification of other genes in particular encoding target proteins.

Stage 1: Preparation of the gp12 Gene

The gp12 gene is amplified by PCR starting from the genomic DNA of wild-type T4 obtained from a concentrated culture of phage lysate (see above) using as primers

```
gp12F 5'-TGAGTAATAATACATATCAACACG,   (SEQ ID No. 2)
and
gp12R 5'-TGATTCTTTTACCTTAATTATGTAC.  (SEQ ID No. 3)
```

After purification on preparative agarose gel, the PCR product (gp12A) is used as the matrix in error-prone PCR reactions with the aim of introducing point mutations and insertions in the coding region corresponding to the receptor binding domain of gp12 (see FIG. 5).

Stage 2: Introduction of Random Mutations in the Receptor Binding Domain

A series of 4 nested PCR reactions (each of 40 cycles) is carried out in the presence of Mn2 so as to induce random polymerase errors.

The error-prone PCRs are carried out in a reaction volume of 100 µl, using matrices and primers at final concentrations respectively equal to 400 ng and 30 µmol, with 0.2 mM of dATP and dGTP (of each), 1 mM of dCTP and dTTP (of each), 2.5 mM of $MgCl_2$, 0.7 mM of $MnCl_2$ and 5 U of DNA-polymerase Taq (New England Biolabs, Inc.) in reaction buffer 1×. PCR is carried out at 96° C. for 2 min, with 30 cycles at 95° C. for 1 min, 56° C. for 1 min and 72° C. for 2 min, and a final extension at 72° C. for 7 min.

The first reaction (P1-1) uses as primers:

```
p12NF1F 5'-TCAAGGTAACCGCATCGTAAC    (SEQ ID No. 4)
p12NF2R 5'-AAAGACCACGCATGTCAG       (SEQ ID No. 5)
```

The second reaction (P2-1) uses as primers:

```
p12NF2F 5'-TGCCATGGTGGAACTGTTCA     (SEQ ID No. 6)
p12NF3R 5'-CACCTAATCTAGGTTTAC       (SEQ ID No. 7)
```

The third reaction (P3-1) uses as primers:

```
p12NF3F 5'-CTGACATGCGTGGTCTTT       (SEQ ID No. 8)
P12NF4R 5'-ATGTTTATGATAAGACAT       (SEQ ID No. 9)
```

The fourth reaction (P4-1) uses as primers:

```
p12NF4F 5'-GTAAACCTAGATTAGGTG       (SEQ ID No. 10)
p12NF5R 5'-TCATTCTTTTACCTTAATTAT    (SEQ ID No. 11)
```

Each of these reaction products displays a partial overlap with two other reaction products and the primers used correspond to constant domains conserved in protein gp12. These domains must be faithfully preserved in the final mutated gene structures produced. However, some of the fragments produced by the error-prone PCR reactions might well have undergone mutagenesis in these regions. In order to preserve intact domains, each of the aforementioned products must then be submitted to high-fidelity PCR reactions with the aim of selective amplification of only the fragments in which the conserved domain was retained.

Stage 3: Selective Amplification of the Desired Fragments

This is effected by two series of high-fidelity PCR reactions, each comprising 25 cycles.

The high-fidelity PCRs are carried out in a reaction volume of 50 µl, using matrices and primers at final concentrations respectively equal to 250 ng and 40 pM, in buffer for pfu 1×(Tris-HCl 20 mM at pH 9.0, KCl 10 mM, $MgSO_4$ 1 mM, $(NH_4)_2SO_4$ 6 mM, 0.1% of Triton X-100, 0.1 mg/ml of SAB) with 200 µM of dNTP and 5 U of pfu polymerase (Promega). The PCR profiles are as follows: 94° C. for 20 s, 45° C. for 15 s and 72° C. for 30 s, with repetition for 20 cycles.

In the first series of reactions (P1-2 to P4-2), an aliquot (about 250 ng) of each of the aforementioned PCR products is amplified using the corresponding "F" primers (for example: p12NF1F) biotinylated at the 5' end. This is necessary for separating the desired products from the matrices that cannot be amplified (mutated conserved domains) which have practically identical lengths and cannot be separated by gel electrophoresis.

The products from each reaction are then passed through size-exclusion minicolumns (to remove the excess of primers), purified individually on streptavidin beads, washed in binding buffer, eluted, precipitated and resuspended in $ddH_2O$.

In the second series of reactions, an aliquot of the purified reaction products P1-2 is mixed with an equal quantity of reaction products P2-2. They have the priming site F2-R1 and F3-R2 in common. Consequently, the "−" strand of the products of reaction P2-2 serves as primer for the "+" strand of the products of reaction P1-2 and extension with a polymerase begins at the inner priming site F2-R1 of P1-2. Extension fails for the products of reaction P1-2 where this conserved site was mutated significantly.

Similarly, the "+" strand of the products of reaction P1-2 serves as primer for the "−" strand of the products of reaction P2-2 and extension with a polymerase begins at the inner priming site F3-R2 of P2-2. Extension fails for the products of reaction P2-2 where this conserved site was mutated significantly.

The PCR products amplified successfully (PA-1) correspond to fusion of fragments P1-2 and P2-2 in which each of the four conserved domains (F1+F2-R1+F3-R2+F4-R3) was retained in the non-mutated state.

A similar mixture is prepared from the products of reaction P3-2 and P4-2. In these reactions, successful extension is based on intact inner conserved sites F4-R3 (P3-2) and F5-R4 (P4-2) and the resultant PCR products (PA-1 and PB-1) correspond to fusion of fragments P3-2 and P4-2 in which each of the four conserved domains (F3-R2+F4-R3+F5-R4+R5) was obtained in the non-mutated state.

The products obtained are purified by preparative gel electrophoresis as the dimensions of the fused PCR products are very different from those of the individual matrices.

In order to increase the yield in this second series of PCR reactions, the extension protocol can be modified as follows:

10 cycles with only the products P1-2 and P2-2, and P3-2 and P4-2 in the reaction mixtures.

The reactions are interrupted, 50 ng of each of the primers p12NF1F and p12NF3R is added to mixture PA-1 whereas 50 ng of each of the primers p12NF3F and p12NF5R is added to mixture PB-1, then the PCR reactions are allowed to continue for 15 additional cycles.

Stage 4: Reconstitution of the Mutated Anchoring Domain of gp12

After purification, equal aliquots of the products PA-1 and PB-1 are used together in a high-fidelity PCR reaction comprising 30 cycles for the purpose of reconstituting the complete receptor binding domain of gp12 in unique fragments containing the various mutations introduced above.

In this case, as in the preceding series of reactions, products PA-1 serve as extension primers for products PB-1 and vice versa.

The final fused PCR product (gp12BD-Fu) is purified by gel electrophoresis as its dimensions are very different from those of the individual matrices.

In order to increase the yield, the extension protocol can be modified by proceeding to a reaction comprising 15 cycles with only the products P1-2 and P2-2, and P3-2 and P4-2 in the reaction mixtures. The reactions are interrupted, 50 ng of each of the primers p12NF1F and p12NF5R is added to the mixture, then the PCR reactions are allowed to continue for 15 additional cycles.

After purification, an aliquot (about 250 ng) of the reconstituted receptor binding domain of gp12 is used as matrix in a new series of four error-prone PCR reactions, followed by selective amplifications and reconstitutions of the domains in the manner described above.

However, since, at each fusion stage (stages 3 and 4 above), all the possible mutations introduced individually in each sub-domain are mixed randomly in the final reconstituted receptor binding domain, there are limits as to the number of cycles of mutagenesis that can be carried out without an adverse effect on the conserved domains. In view of the necessary stages of selective amplification, it is considered that, beyond 4 successive cycles, all the mutations newly introduced will have a strong probability of an adverse effect on a conserved domain or of introduction of a reversion restoring the original, non-mutated sequence T4.

Stage 5: Reconstitution of the Modified Copy of the gp12 Gene in its Entirety

1) Amplification of the Segment of gp12 Upstream of the Receptor Binding Domain.

The gp12 gene, generated by PCR, produced above (gp12A) is used as matrix together with the primers

```
gp12F   5'-TGAGTAATAATACATATCAACACG, (SEQ ID No. 12)
and gp12AR  5'-GTTACGATGCGGTTACCTTGT     (SEQ ID No. 13)
```

This is followed by purification of the amplification products obtained on preparative agarose gel, precipitation then resuspension in ddH$_2$O.

2) Amplification of the Mutated Binding Domain of gp12

An aliquot (about 500 ng) of the PCR product (gp12B) is used together with an equal quantity of reconstituted receptor binding domain of gp12 (gp12BD-Fu) in a high-fidelity PCR reaction. It should be noted that these two products only have an overlap of 20 bp in common. Consequently, the profile of the PCR reaction must be modified to take this into account.

Modified PCR profile: A) 30 min at 96° C. then 5 cycles of 1 min at 94° C., and 10 s at 45° C., and then B) 5 cycles of 1 min at 94° C. and 20 s at 50° C., then C) 5 cycles of 1 min at 94° C., 30 s at 50° C., and finally D) 15 cycles of 1 min at 94° C., 1 min at 55° C., and 5 seconds at 72° C.

In order to increase the yield, the reaction can be interrupted at sub-stage D above and the primers gp12F and p12NF5R can be introduced into the mixture. Then the reaction is left to resume and to go to completion.

The final products (gp12-Mut) are purified on preparative agarose gel, precipitated and resuspended in ddH$_2$O until they are used.

Stage 6: Verification by Sequencing of the PCR Products gp12-Mut Obtained

Figure 6:
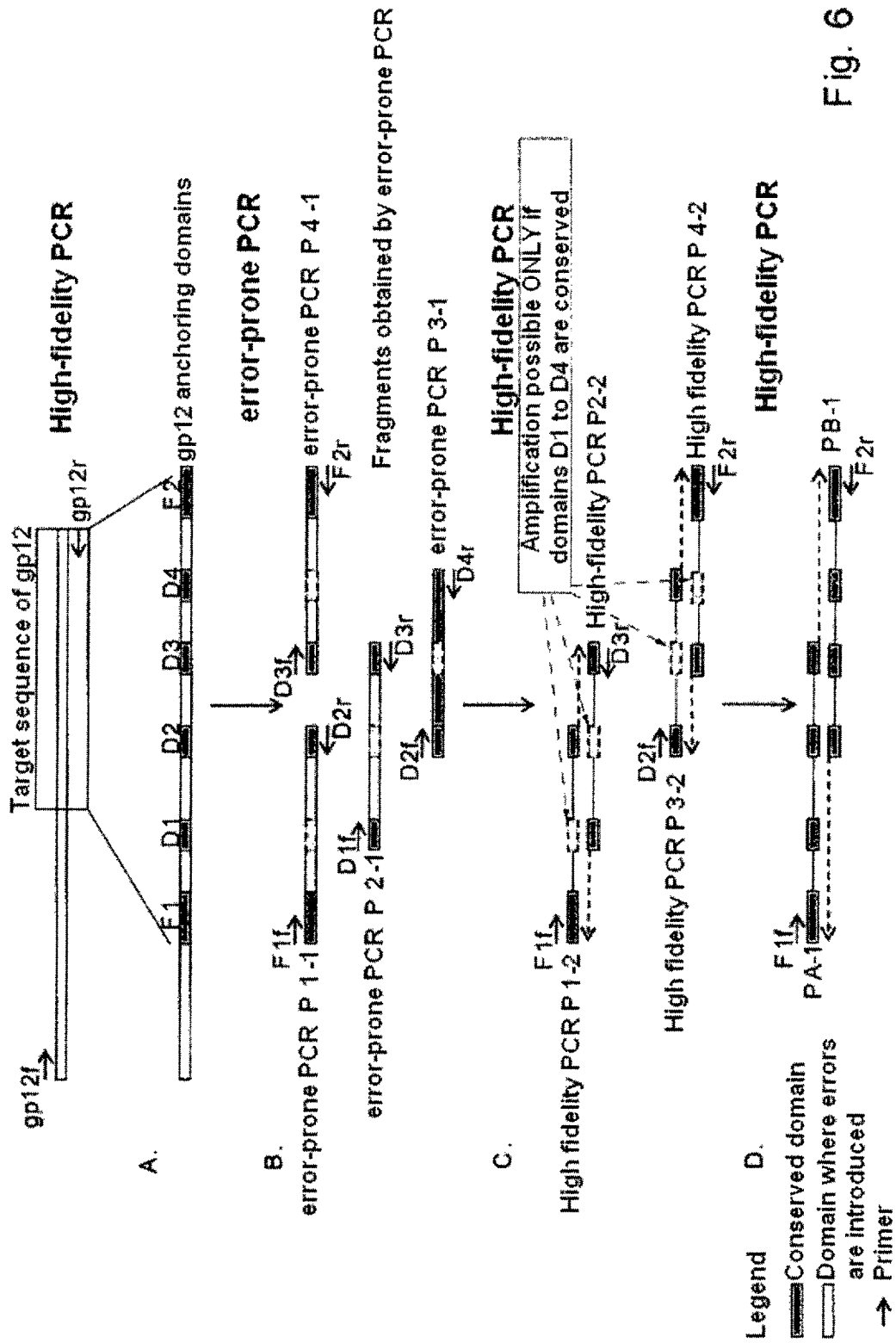

The PCR products purified on agarose gel are sequenced using an automatic sequencer in order to verify that mutations have indeed been introduced randomly in gp12, while preserving domains D1 and D2 intact. Sequencing is carried out on two portions corresponding respectively to nucleotides 1089 to 1110 (FIG. 6A) and 1195 and 1212 (FIG. 6B) of gp12 (SEQ ID No. 1). The sequencing profiles obtained are shown in FIG. 6. On comparing the profiles of the PCR products with those of the original sequence of gp12, it is found that numerous additional peaks are added to the expected profile of gp12. These additional peaks reflect a high frequency of mutations introduced in the sequence by the PCR method. These peaks are not found for domain D1, confirming that this domain has preserved its sequence identity with that of gp12.

Cloning of the Mutated gp12-Mut in an Alternative Vector for Homologous Recombination The procedures stated above made it possible to generate, in a manner similar to gp12, the mutant genes gp37 and gp38 of T4.

The purpose of the next procedures is then to introduce these variant genes of T4 in such a way as to promote their introduction, by homologous recombination, in the genome of bacteriophage T4 so as to produce descendants of T4 having host targeting specificities different from that of the parent bacteriophage.

To this end, the mutated genes generated above must be introduced in alternative vectors (a different vector for each gene). In the present case, the vectors pACYC184, pBAD18-K and RR1 are used for cloning each of the mutated genes.

The vector chosen (for example pACYC184 for the cloning of gp12Mut) is cut at the level of site Sma I, purified and resuspended in 20 µl of ddH$_2$O and mixed with the PCR product gp12Mut in a ratio of 1:3. After ligation, the DNA is purified, resuspended in ddH$_2$O and transformed in "electrocompetent" cells DK8 (ATCC 47038). This vector bears a chloramphenicol resistance gene (Chl). Thus, after electroporation and a recovery period of 1 h, the cells are transferred to 10 ml of LB medium containing 170 µg/ml of chloramphenicol and are cultured at 30° C. for 4 h with constant aeration. Then the cells are spread on plates of LB medium+Chl and cultured overnight at 30° C. Some colonies are taken for PCR verification of the presence of the insertion segment gp12Mut and some positive colonies are cultured in LB medium+Chl for the preparation of a concentrated cell culture (DK8-p12C).

Introduction of the Mutated Genes gp37 and gp38 into the Host Bacterium

A fresh one-night culture of DK8-p12C is used for preparing electrocompetent cells.

The vector pBAD18-K is cut at the level of site Sma I, purified and resuspended in 20 µl of ddH$_2$O and mixed with the PCR product gp37Mut in a ratio of 1:3. After ligation, the DNA is purified, resuspended in ddH$_2$O and transformed in "electrocompetent" cells DK8-p12C.

The vector used in this case bears a kanamycin resistance gene (Kan). Thus, after electroporation and a recovery period of 1 h, the cells are transferred to 10 ml of LB medium containing 170 µg/ml of chloramphenicol and 50 µg/ml of kanamycin and are cultured at 30° C. for 4 h with constant aeration. Then the cells are spread on plates of LB medium+Chl+Kan and cultured overnight at 30° C. Some colonies are taken for PCR verification of the presence of the insertion segments gp12Mut and gp37Mut and some positive colonies are cultured in LB medium+Chl+Kan for the preparation of a concentrated cell culture (DK8-p12C-p37K).

A fresh one-night culture of DK8-p12C-p37K is used for preparing electrocompetent cells. The vector RR1 is cut at the level of site Sma I, purified and resuspended in 20 µl of ddH$_2$O and mixed with the PCR product gp37Mut in a ratio of 1:3. After ligation, the DNA is purified, resuspended in ddH$_2$O and transformed in "electrocompetent" cells DK8-p12C-p37K. The vector used in this case bears an ampicillin resistance gene (Amp). Thus, after electroporation and a recovery period of 1 h, the cells are transferred to 10 ml of LB medium containing 170 µg/ml of chloramphenicol+50 µg/ml of kanamycin+60 µg/ml of ampicillin and are cultured at 30° C. for 4 h with constant aeration. Then the cells are spread on plates of LB medium+Chl+Kan+Amp and cultured overnight at 30° C. Some colonies are taken for PCR verification of the presence of the insertion segments gp12Mut, gp37Mut and gp38Mut and some positive colonies are cultured in LB medium+Chl+Kan+Amp for the preparation of a concentrated cell culture (DK8-p12C-p37K-P38A).

It now remains to construct a host capable of exhibiting an extremely effective recombination potency.

Construction of E. coli "Mini-λ" Host Bacteria

To obtain effective recombination of the donor DNA in recA$^+$ or recA$^-$ backgrounds, we prepare the host E. coli which contains a prophage λ bearing the recombination genes exo, bet and gam under the control of a temperature-sensitive repressor cl of λ. The genes exo, bet and gam can easily be activated at 42° C. and inhibited at 32° C. When the λ functions are activated for a period reduced to 5 min, the cells become more recombinogenic and absorb the linear DNA without destroying it. λ Gam inhibits attack on the linear DNA by the nuclease RecBCD of E. coli, and Exo and Beta generate recombination activity for this linear DNA. More importantly, this recombination is effective with DNA homologies limited to 30 to 50 bp at the ends of substrates consisting of linear DNA.

The oligonucleotides 5' GTATGCATGCTGGGTGTGG (MλRf) and 5' CGCACTCTCGATTCGTAGAGCCTCG (MλRr) are used as primers for the PCR amplification of the DNA from the region attP-cro using the DNA of λ cl857 as matrix.

Once the prophage λ has been generated by PCR, one possibility consists of cloning the prophage λ in the small copy number plasmid pFN476 (ATCC86962) with selection by LacZ, for example.

The vector pFN476 is cut at the level of site Sma I (free end), purified, resuspended in 20 µl of ddH$_2$O and mixed with the PCR product of prophage λ in a ratio of 1:3. After ligation, the DNA is purified, resuspended in ddH$_2$O and transformed in "electrocompetent" cells DK8-p12C-p37K-p38A. After recovery, the cells are spread on plates of LB medium X-gal+Chl+Kan+Amp (see above) and incubated at 30° C.

Some blank colonies are selected for the PCR verification of the presence of prophage λ. A colony positive for prophage λ is then cultured overnight at 30° C. in LB medium+Chl+Kan+Amp for preparing a concentrated cell culture (DK8-T4Mut-λ) to be used in further manipulations.

At this stage, the transformed hosts are inducible by λ at elevated temperature, lacZ-positive and contain copies of mutated genes gp12, gp37 and gp38 of T4 ready for homologous recombination.

Production of the Descendants of Bacteriophage T4 with Extended Host Ranges

A fresh one-night culture of cells DK8-T4Mut-λ is prepared in LB medium+Chl+Kan+Amp at 30° C.

The cultures for infection by T4 are started with a volume less than or equal to 0.05 ml of cells from a one-night culture for 10 ml of LB medium+Chl+Kan+Amp in order to guarantee that the cells move on to the exponential growth phase before adding the bacteriophage.

To improve the aeration, these cultures are multiplied in 250-ml side-branch Erlenmeyer flasks, stoppered non-hermetically, in a water bath of a shaker at 30° C.

250 ml of cells in LB medium+Chl+Kan+Amp are cultured at a density of 3×10$^8$ cells per ml at 30° C. with shaking.

Aliquots of 10 ml of cells in exponential growth are then transferred to 40 ml of LB medium+Chl+Kan+Amp preheated to 42° C. and incubated for exactly 15 min at 42° C. with constant aeration. Tryptophan is added at a concentration of 0.02 mg/ml and followed by bacteriophage T4 at a multiplicity of about 10 particles per cell. The cultures are transferred to a water bath at 30° C., leaving growth to continue for exactly 25 min.

The aim in this case is to isolate the descendants of the first round and to halt propagation before these first-generation bacteriophage descendants have had time to transform to reproducers.

Recovering the Descendants of the Bacteriophages

The cells are collected by centrifugation at 5000 rpm for 5 minutes and the supernatant is recovered, some drops of chloroform are added and the mixture is centrifuged again for 10 min at 6000 rpm. The supernatant, excluding the chloroform, is adjusted to a concentration of buffer SM 1×(MgSO₄ 10 mM, NaCl 100 mM, 0.01% of gelatin and Tris-HCl 50 mM [pH 7.5]) using buffer concentrated 5×, and is stored at 4° C. before analysis.

The cells collected in a pellet are resuspended in 8 ml of solution of Tris-hydrochloride 0.05 M at pH 8.0 with 25% saccharose. An aliquot of 1.6 ml of lysozyme (5 mg/ml) is added and the mixture is incubated for 5 min at 0° C. An aliquot of 3.2 ml of solution of EDTA 0.2 M is added and the mixture is incubated for an additional period of 15 min at 0° C. The cell lysate is adjusted to 500 mM of Tris-HCl at pH 7.4, 100 mM of MnCl₂ by means of buffer concentrated 10×, equilibrated at 15° C. and incubated with 10 U of Dnase1 (Sigma) for 2 h. The mixture is then centrifuged at 6000 rpm for 10 min. The clear supernatant is cautiously removed, adjusted to a concentration of buffer SM 1× and stored as described previously.

Verification of the Extensions of the Host Ranges

Cultures of pathogenic bacterial strains (*Yersinia* sp., *Salmonella* sp., *E. coli* 0157 H7, *Enterobacter sakazakii*, etc.) are prepared.

Aliquots of 3 ml are then infected with 1 ml of concentrated culture of the descendants and incubated at 30° C. with stirring. The turbidity of the culture is determined by colorimetry immediately after infection and then every 60 min. A significant drop in culture turbidity in a time of 5 hours indicates that the particles capable of infecting the test host were present in the recombinant descendants of T4. Some drops of chloroform are added to the culture or cultures, which causes a clear decrease in turbidity, and the cultures are then centrifuged at 5000 rpm for 5 min.

The supernatant is recovered and used as infectious substance for the production of particles of bacteriophages dedicated to the bacterium tested, which in nature, cannot be attacked by the wild-type bacteriophage T4.

The invention claimed is:

1. A method for producing a diversified nucleotide sequence by PCR, comprising;
   i) performing an error prone PCR reaction on the whole of nucleotide sequence S, wherein said sequence is delimited at its 5' and 3' ends by two segments F1 and F2, using at least two primers, one of said primers is a sense strand and the other an antisense strand of segments F1 and F2, respectively, so as to amplify sequence S and introduce random mutations;
   ii) purifying the amplification products obtained in stage i);
   iii) performing a high-fidelity PCR reaction starting from the amplification products purified in stage ii), using as sense and antisense primer pairs at least:
      a sense primer corresponding to F1 and an antisense primer of $D_N$, to amplify region F1-$D_N$ of S and preserve the identity of segment $D_N$, and
      an antisense primer corresponding to F2 and a sense primer corresponding to $D_{N-1}$, to amplify region $D_{N-1}$-F2 of S and preserve the identity of segment $D_{N-1}$,
   wherein the primers corresponding to segment $D_N$ and $D_{N-1}$ hybridize with the whole of $D_N$ and $D_{N-1}$, respectively;
   iv) purifying the amplification products obtained in stage iii);
   v) performing a high-fidelity PCR reaction starting from the amplification products purified in stage iv), using at least one pair of sense and antisense primers F1 and F2; and
   vi) purifying the amplification products obtained in stage v),
   wherein the identity of at least N inner domains $D_N$ and $D_{N-1}$ of said nucleotide sequence S are preserved.

2. The method according to claim 1, wherein sequence S is a genetic sequence encoding a protein of interest.

3. The method according to claim 2, wherein the protein of interest is a target protein of a bacteriophage.

4. The method according to claim 2, wherein the protein of interest is a ligand protein.

5. The method according to claim 2, wherein the protein of interest is an immunoglobulin.

* * * * *

SEQUENCE LISTING

```
<160> NUMBER OF SEQ ID NOS: 13

<210> SEQ ID NO 1
<211> LENGTH: 1582
<212> TYPE: DNA
<213> ORGANISM: bacteriophage T4
<220> FEATURE:
<221> NAME/KEY: misc_feature
<222> LOCATION: (1)..(1582)
<223> OTHER INFORMATION: Coding region of the gp12 gene bacteriophage T4

<400> SEQUENCE: 1
gagtaataat acatatcaac acgtttctaa tgaatctcgt tatgtaaaat ttgatcctac      60
cgatacgaat tttccaccgg agattactga tgttcacgct gctatagcag ccatttctcc     120
tgctggagta aatggagttc ctgatgcatc gtcaacaaca aagggaattc tatttattcc     180
cactgaacag gaagttatag atggaactaa taataccaaa gcagttacac cagcaacgtt     240
ggcaacaaga ttatcttatc caaatgcaac tgaaactgtt tacggattaa caagatattc     300
aaccaatgat gaagccattg ccggagttaa taatgaatct tctataactc cagctaaatt     360
tactgtcgcc cttaataatg cgtttgaaac gcgagtttca actgaatcct caaatggtgt     420
tattaaaatt tcatctctac cgcaagcatt agctggtgca gatgatacta ctgcaatgac     480
tccattaaaa acacagcagt tagctattaa attaattgcg caaattgctc cttctgaaac     540
cacagctacc gaatcggacc aaggtgttgt tcaattagca acagtagcgc aggttcgtca     600 gggaactta agagaaggct atgcaatttc tccttatacg tttatgaatt catcttctac      660
tgaagaatat aaaggcgtaa ttaaattagg aacacaatca gaagttaact cgaataatgc     720
ttctgttgcg gttactggcg caactcttaa tggtcgtggt tctacgacgt caatgagagg     780
cgtagttaaa ttaactacaa ccgccggttc acagagtgga ggcgatgctt catcagcctt     840
agcttggaat gctgacgtta tccagcaaag aggtggtcaa attatctatg gaacactccg     900
cattgaagac acatttacaa tagctaatgg tggagcaaat attacgggta ccgtcagaat     960
gactggcggt tatattcaag gtaaccgcat cgtaacacaa aatgaaattg atagaactat    1020
tcctgtcgga gctattatga tgtgggccgc tgatagtctt cctagtgatg cttggcgctt    1080
ctgccatggt ggaactgttt cagcgtcaga ttgtccatta tatgcttcta gaattggaac    1140
aagatatggc ggaaacccat caaatcctgg attgcctgac atgcgtggtc tttttgttcg    1200
tggttctggt cgtggttctc acttaacaaa tccaaatgtt aatggtaatg accaatttgg    1260
```

```
taaacctaga ttaggtgtag gttgtaccgg tggatatgtt ggtgaagtac agatacaaca    1320
gatgtcttat cataaacatg ctggtggatt tggtgagcat gatgatctgg gggcattcgg    1380
taatacccgt agatcaaatt ttgttggtac acgtaaagga cttgactggg ataaccgttc    1440
atacttcacc aatgacggat atgaaattga cccagaatca caacgaaatt ccaaatatac    1500
attaaatcgt cctgaattaa ttggaaatga aacacgtcca tggaacattt ctttaaacta    1560
cataattaag gtaaaagaat ga                                              1582
```

```
<210> SEQ ID NO 2
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger gp12F amplified the gene Gp12 of
      bacteriophage T4

<400> SEQUENCE: 2
tgagtaataa tacatatcaa cacg                                              24
```

```
<210> SEQ ID NO 3
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger gp12R amplified the gene Gp12 of
      bacteriophage T4

<400> SEQUENCE: 3
tgattctttt accttaatta tgtac                                             25
```

```
<210> SEQ ID NO 4
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF1F nternal anchor domain for gp12
      bacteriophage T4

<400> SEQUENCE: 4
tcaaggtaac cgcatcgtaa c                                                 21
```

```
<210> SEQ ID NO 5
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF2F internal anchor domain for gp12
      bacteriophage T4

<400> SEQUENCE: 5
aaagaccacg catgtcag                                                     18
```

```
<210> SEQ ID NO 6
<211> LENGTH: 20
```

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF2F internal anchor domain for gp12
      bacteriophage T4

<400> SEQUENCE: 6
tgccatggtg gaactgttca                                                  20

<210> SEQ ID NO 7
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF3R internal anchor domain for gp12
      bacteriophage T4

<400> SEQUENCE: 7
cacctaatct acgtttac                                                    18

<210> SEQ ID NO 8
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF3F internal anchor domain for gp12
      bacteriophage T4

<400> SEQUENCE: 8
ctgacatgcg tggtctttt                                                   18

<210> SEQ ID NO 9
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF4R internal anchor domain for gp12
      bacteriophage T4

<400> SEQUENCE: 9
atgtttatga taagacat                                                    18

<210> SEQ ID NO 10
<211> LENGTH: 18
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF4F internal anchor domain for gp12
      bacteriophage T4

<400> SEQUENCE: 10
gtaaacctag attaggtg                                                    18

<210> SEQ ID NO 11
<211> LENGTH: 21
```

-continued

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger P12NF5R internal anchor domain for gp12
      bacteriophage T4

<400> SEQUENCE: 11
tcattctttt accttaatta t                                              21

<210> SEQ ID NO 12
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger gp12F amplified the gene Gp12 of
      bacteriophage T4

<400> SEQUENCE: 12
tgagtaataa tacatatcaa cacg                                           24

<210> SEQ ID NO 13
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Trigger gp12F amplified the gene Gp12 of
      bacteriophage T4

<400> SEQUENCE: 13
gttacgatgc ggttaccttg t                                              21
```